United States Patent
Tang et al.

(10) Patent No.: US 9,227,020 B2
(45) Date of Patent: Jan. 5, 2016

(54) DISPOSABLE REMOTE INJECTION SYRINGE FOR USE WITH AN ENDOSCOPE

(75) Inventors: Xiaowei Tang, Nanjing (CN); Meijuan Chen, Nanjing (CN); Jie Hu, Nanjing (CN); Derong Leng, Nanjing (CN); Fukang Jin, Nanjing (CN)

(73) Assignee: MICRO-TECH (NANJING) CO., LTD., Nanjing (CN)

(*) Notice: Subject to any disclaimer, the term of this patent is extended or adjusted under 35 U.S.C. 154(b) by 0 days.

(21) Appl. No.: 13/984,195

(22) PCT Filed: Feb. 17, 2012

(86) PCT No.: PCT/CN2012/071295
§ 371 (c)(1),
(2), (4) Date: Aug. 7, 2013

(87) PCT Pub. No.: WO2013/107068
PCT Pub. Date: Jul. 25, 2013

(65) Prior Publication Data
US 2014/0323991 A1    Oct. 30, 2014

(30) Foreign Application Priority Data
Jan. 18, 2012    (CN) .......................... 2012 1 0014952

(51) Int. Cl.
*A61M 5/32* (2006.01)
*A61B 17/34* (2006.01)
*A61B 1/00* (2006.01)

(52) U.S. Cl.
CPC ................ *A61M 5/3287* (2013.01); *A61B 1/00* (2013.01); *A61B 17/3478* (2013.01)

(58) Field of Classification Search
CPC ........... A61B 17/3478; A61M 5/3202; A61M 5/322; A61M 5/3232; A61M 5/3287
USPC .................................. 604/117, 220
See application file for complete search history.

(56) References Cited

U.S. PATENT DOCUMENTS

| | | | |
|---|---|---|---|
| 5,015,240 A * | 5/1991 | Soproni et al. | 604/192 |
| 5,562,626 A | 10/1996 | Sanpietro | |
| 6,290,683 B1 * | 9/2001 | Erez et al. | 604/273 |
| 2013/0060202 A1 * | 3/2013 | Thorley et al. | 604/220 |

FOREIGN PATENT DOCUMENTS

| | | |
|---|---|---|
| CN | 200720078302.6 | 1/2008 |
| CN | 200810111537 | 12/2008 |
| CN | 201220022642.8 | 11/2012 |

* cited by examiner

*Primary Examiner* — Kami A Bosworth
(74) *Attorney, Agent, or Firm* — Oliff PLC

(57) ABSTRACT

A disposable remote-injection syringe comprises a syringe needle (2), an inner tube (3), an outer tube (4) and a casing (10), the syringe needle (2) being arranged on one end of the inner tube (3), the inner tube (3) being arranged in the outer tube (4), the outer tube (4) being connected with the casing (10).

19 Claims, 7 Drawing Sheets

DISPOSABLE REMOTE INJECTION SYRINGE FOR USE WITH AN ENDOSCOPE

TECHNICAL FIELD

The invention relates to the technical field of medical instruments, in particular to a disposable remote-injection syringe for use with an endoscope. This disposable remote-injection syringe may be applied in the following fields: 1, acute esophageal variceal bleeding; 2, marking of polyps or early cancer parts to be removed prior to the operation and reexamination within a short term after marking; 3, polyp or early cancer part removal postoperative bleeding; 4, vascular damage bleeding in ulcer areas; 5, endoscopic sphincterotomy postoperative bleeding; 6, injection to basilar part of flat polyps or early cancer parts before removal thereof to make the polyps protruded for more accurate removal.

BACKGROUND OF THE INVENTION

An endoscope is a tube equipped with lamplight, so that it may enter the stomach through the oral cavity or enter the body through other natural orifices. Pathological changes which may not be displayed under X-ray may be examined by the endoscope. Therefore, the endoscope is very useful to doctors. For example, with an endoscope, doctors may observe ulcers or tumors inside the alimentary tract, hereby establishing the best therapeutic plans.

The existing injection syringes for use with various endoscopes usually have a slender insertion part capable of inserting into the endoscope channel and an operating part connected with a base end of the insertion part. The insertion part comprises a double-layer tube having an outer tube and an inner tube which may be inserted into the outer tube in a way that it may be fed into and retracted from the outer tube freely. The operating part enables the inner tube to be fed into or retracted from the outer tube. A front end of the inner tube is provided with a hollow syringe needle.

The existing injection syringes usually have a single injection function. When in use, the whole feeding or retracting of the needle needs to be completed by hands, and control by hands of the operators is required during the whole operation. Therefore, the existing injection syringes are laborious and inconvenient to operation.

In addition, for the existing injection syringes for use with an endoscope, the length of the needle tip extending out from a cannula may be determined just before an operation. Once determined, the length cannot be changed during the operation, resulting in that the existing injection syringes are difficult to adapt to different disease parts and the piercing depth of the needle tip cannot be adjusted according to the specific situation of the affected part.

SUMMARY OF THE INVENTION

The technical problem of the invention to be solved is to provide a disposable remote-injection syringe for use with an endoscope, which may be operated by a single hand and automatically locked, and the extension depth of the syringe needle of which may be positioned and adjusted.

The invention employs the following technical solutions.

A disposable remote-injection syringe for use with an endoscope is provided, comprising a syringe needle 2, an inner tube 3, an outer tube 4 and a casing 10. The syringe needle 2 is arranged on one end of the inner tube 3, the inner tube 3 is arranged in the outer tube 4, and the outer tube 4 is connected with the casing 10. The disposable remote-injection syringe for use with an endoscope further comprises an injection plunger rod 11, one end of which extends into the casing 10 to be connected with the casing 10 in a sliding manner. An elastomer 8 connected with the injection plunger rod 11 is arranged in the casing 10. Another end of the inner tube 3 is connected with the injection plunger rod 11. A locking socket 13 is arranged on the casing 10, and a locking plug 112 connected with the locking socket 13 in an engaging manner is arranged on the injection plunger rod 11.

The outer tube 4 is connected with the casing 10 via a positioning cap 6, and one end of the positioning cap 6 is arranged in the casing 10 while another end thereof is connected with a sheath 5 sleeved outside the outer tube 4.

Another end of the inner tube 3 is connected with the injection plunger rod 11 via a boosting tube 9.

The syringe needle 2 and the inner tube 3 form an integral structure which is a complete stainless steel tube. The stainless steel tube serves as the inner tube 3, an end part of the stainless steel tube is a needle tip used as the syringe needle 2.

The injection plunger rod 11 is provided with a protruding trigger 111 on which the locking plug 112 is arranged, and the locking plug 112 is provided with a one-way check rack 113.

The injection plunger rod 11 is provided with an anti-twist body 110 connected with the casing 10 in a sliding manner.

The locking socket 13 comprises a slot 130, an arched elastomer 131 located above the slot 130, a platy-elastomer 132 located below the slot 130 and slot wings 133, and the arched elastomer 131 and the platy-elastomer 132 are connected with each other by the slot wings 133 arranged on two sides. The platy-elastomer 132 is provided with a check hook 134, and clearance slots are arranged on the two sides of the platy elastomer 132.

The arched elastomer 131 is provided with a release button 135.

A tail end of the outer tube 4 is provided with a front end cap 1. The front end cap 1 and the outer tube 4 form an integrated structure or a split structure.

The tail end of the outer tube 4 may also be an enclosed structure, and is provided with a small hole from which the syringe needle is fed or retracted.

A tail end of the injection plunger rod 11 is provided with a syringe adapter 12.

The disposable remote-injection syringe for use with an endoscope further comprises a spring tube 15 arranged on an inner side of the outer tube 4.

The disposable remote-injection syringe for use with an endoscope further comprises a needle spring 14 arranged on a far end of the inner tube 3 and sleeved on the syringe needle 2.

The disposable remote-injection syringe for use with an endoscope further comprises a needle spring 14 arranged on the front end cap 1.

The disposable remote-injection syringe for use with an endoscope of the invention has the following advantages.

1. The disposable remote-injection syringe for use with an endoscope of the invention is ingenious in structure, simple in production and reliable in accuracy. The locking plug and the locking socket both are integrally formed. Inserting, fastening and releasing may be achieved by virtue of elasticity and strength of materials per se.

2. The disposable remote-injection syringe for use with an endoscope of the invention is convenient to operate, and may be operated by a single hand. When grasping the casing, an operator may insert the locking plug into the locking socket after pressing the trigger down by the thumb or index finger to achieve automatic self-locking and positioning via the check hook and a reversed rack, and press the release button down by a single hand to make the syringe needle automatically retracted under the action of the elastomer without manually pulling it back, thereby overcoming the defect that the existing injection syringes need to be operated by two hands or are complicated and inconvenient to be operated by a single hand.

3. Different from the conventional small handle, the injection syringe of the invention is ergonomically designed and may be grasped easily. Anti-slip ribs are provided on the force application part, thus increasing the sense of touch and preventing slipping. The operation is labor saving and will not be affected even when the operator wears gloves.

Figure 1:
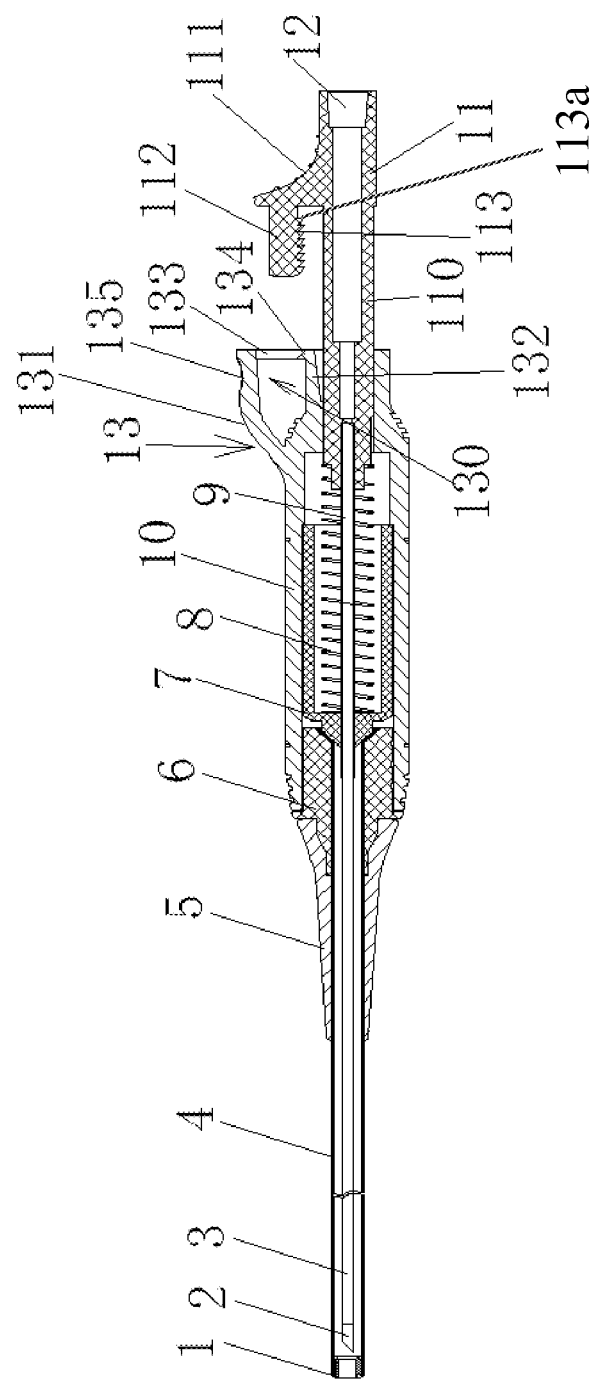
FIG. 1 is a sectional structure diagram of the invention.
Figure 2:
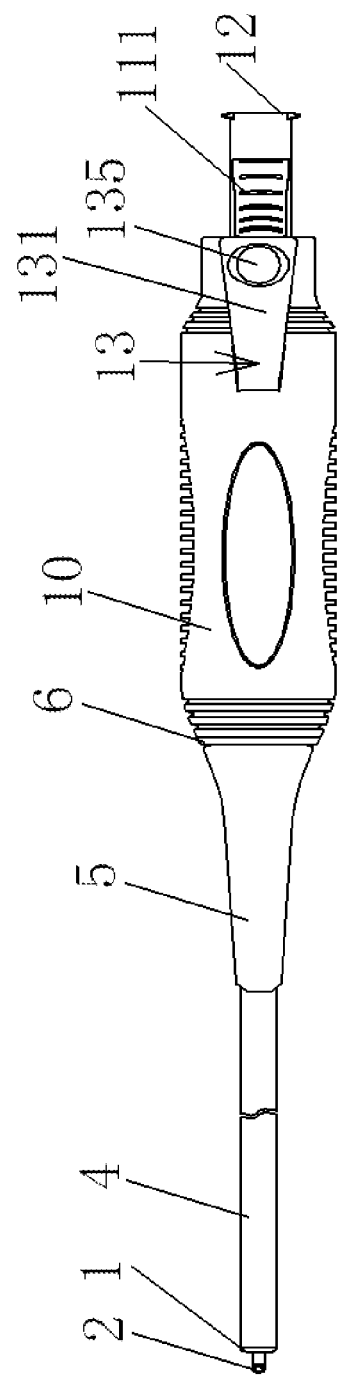
FIG. 2 is an overall structure diagram of the invention.
Figure 3:
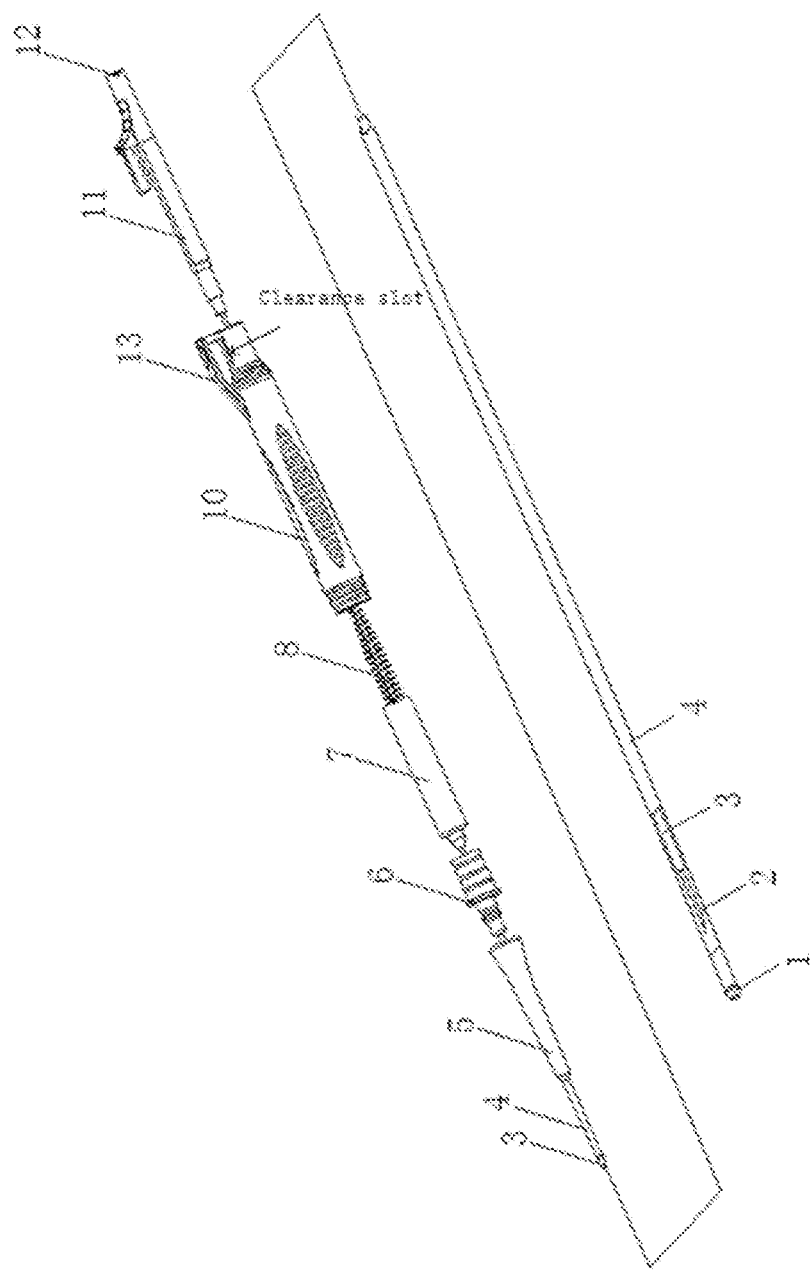
FIG. 3 is an exploded three-dimensional structure diagram of the invention.
Figure 4:
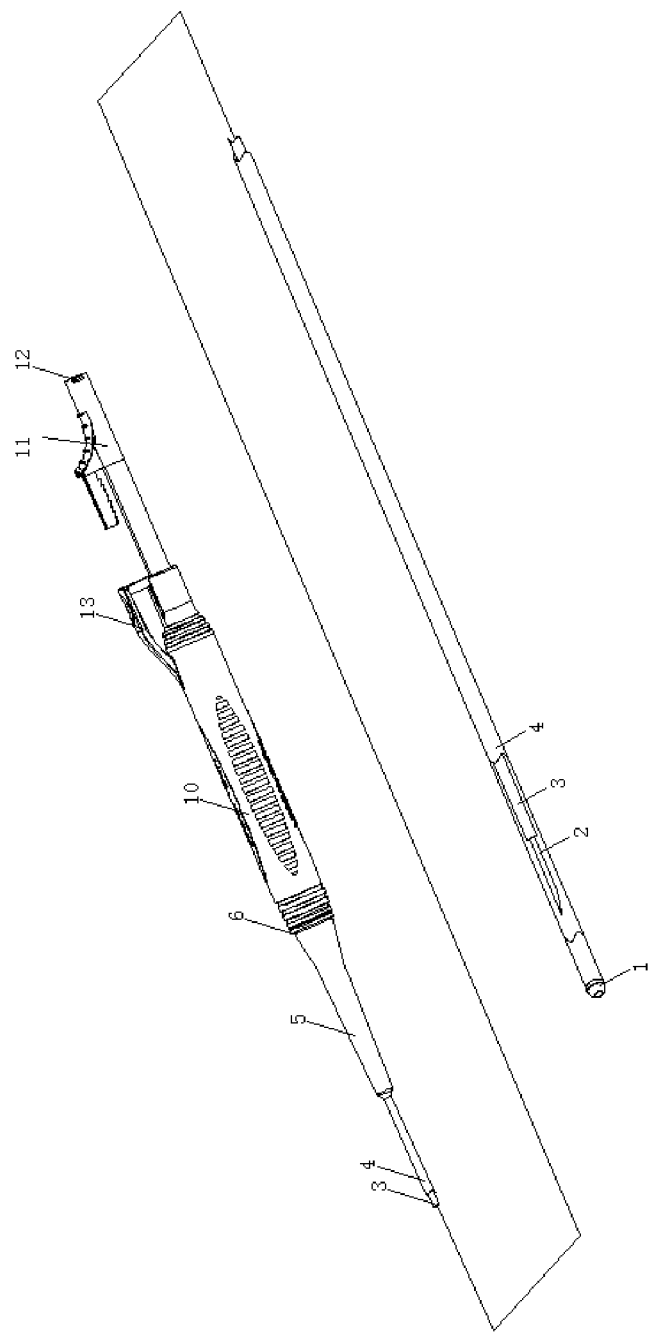
FIG. 4 is a structure diagram of the invention where a syringe needle does not extend out.
Figure 5:
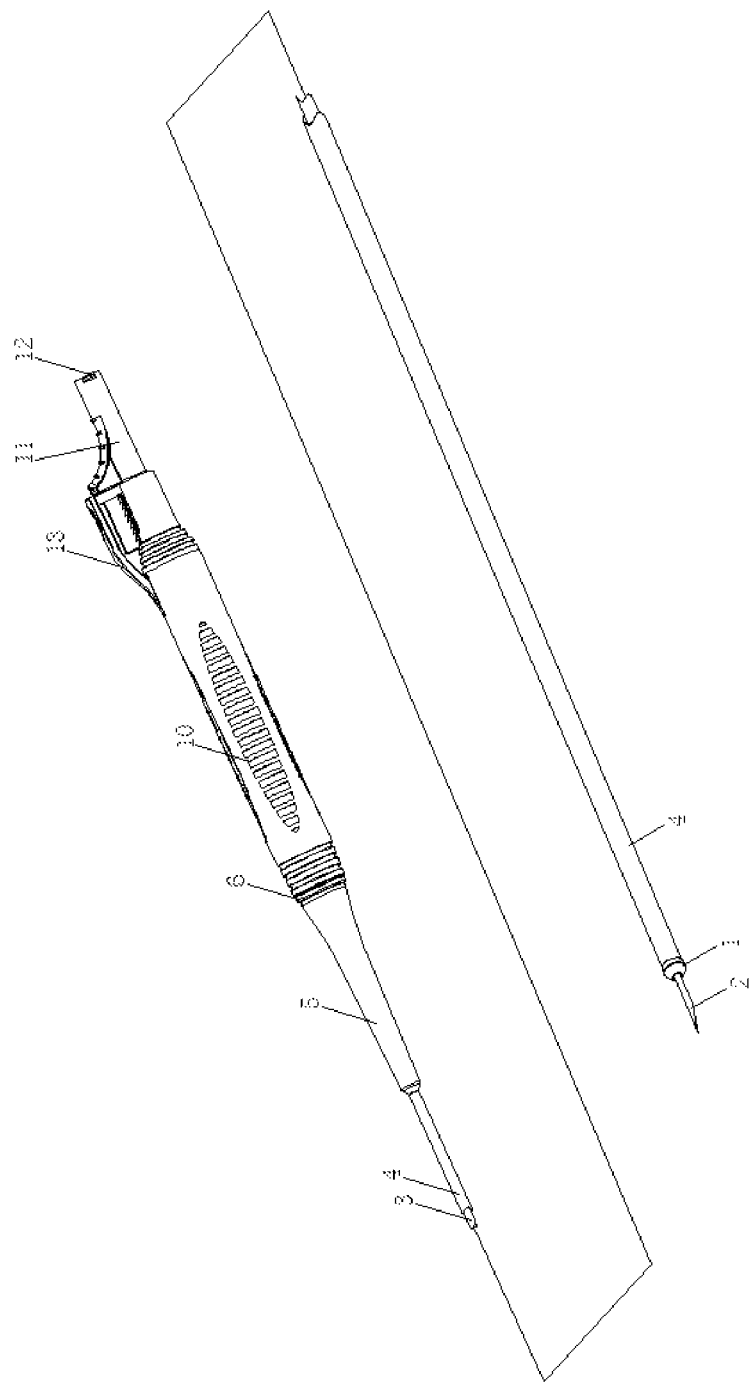
FIG. 5 is a structure diagram of the invention where the syringe needle extends out.
Figure 6:
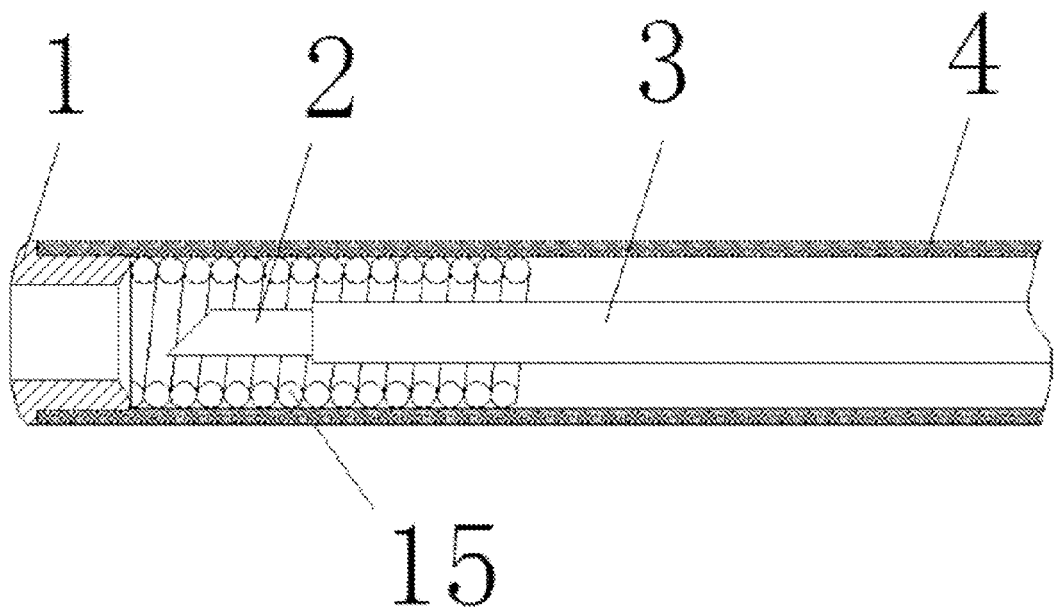
FIG. 6 is a structure diagram of the invention provided with a needle spring tube.
Figure 7:
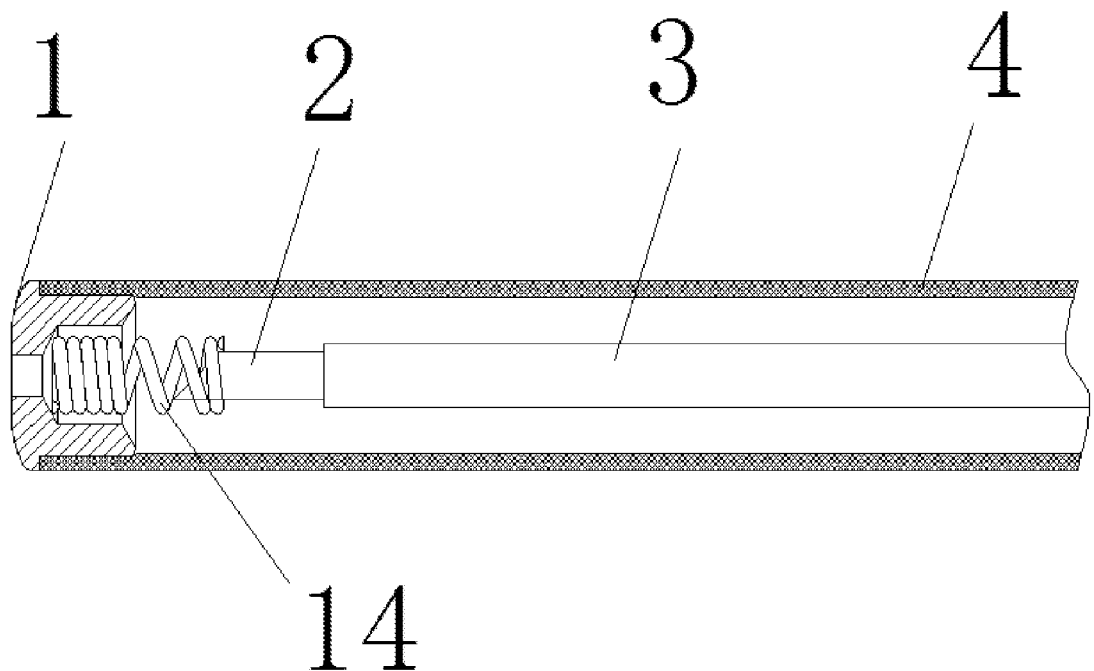
FIG. 7 is a structure diagram 1 of the invention provided with a needle spring.
Figure 8:
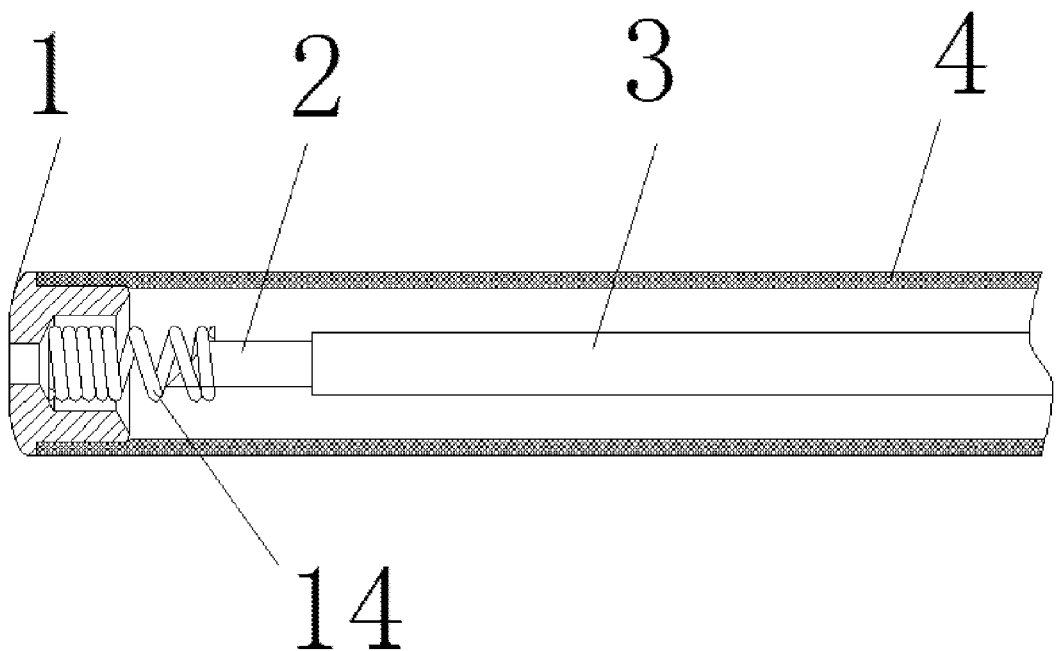
FIG. 8 is a structure diagram 2 of the invention provided with the needle spring; and,
FIG. 9 is a structure diagram of the invention where a front end cap and an outer tube are integrated.

In the drawings: 1—Front end cap; 2—Syringe needle; 3—Inner tube; 4—Outer tube; 5—Sheath; 6—Positioning cap; 7—Support tube; 8—Elastomer; 9—Boosting tube; 10—Casing; 11—Injection plunger rod; 110—Anti-twist body; 111—Trigger; 112—Locking plug; 113—Check rack; 12—Syringe adapter; 13—Locking socket; 130—Slot; 131—Arched elastomer; 132—Platy elastomer; 133—Slot wing; 134—Check hook; 135—Release button; 14—Needle spring; 15—Spring tube.

DETAILED DESCRIPTION OF THE INVENTION

The invention will be further described as below with reference to drawings:

As shown in FIG. 1 to FIG. 5, a disposable remote-injection syringe for use with an endoscope is provided, comprising a syringe needle 2, an inner tube 3, an outer tube 4 and a casing 10. The syringe needle 2 is arranged on one end of the inner tube 3, the inner tube 3 is arranged in the outer tube 4, and the outer tube 4 is connected with the casing 10. The disposable remote-injection syringe further comprises an injection plunger rod 11, one end of which extends into the casing 10 to be connected with the casing 10 in a sliding manner. An elastomer 8 connected with the injection plunger rod 11 is arranged in the casing 10. Another end of the inner tube 3 is connected with the injection plunger rod 11. A locking socket 13 is arranged on the casing 10, and a locking plug 112 connected with the locking socket 13 in an engaging manner is arranged on the injection plunger rod 11.

The outer tube 4 is connected with the casing 10 via a positioning cap 6, and one end of the positioning cap 6 is arranged in the casing 10 while another end thereof is connected with a sheath 5 sleeved outside the outer tube 4.

Another end of the inner tube 3 is connected with the injection plunger rod 11 via a boosting tube 9. The boosting tube 9 is made of hard materials, thus overcoming the problem that propulsive force applied by the injection plunger rod 11 is difficult to be transferred forward via the flexible inner tube 3.

The structure of the boosting tube 9 mentioned above may not be adopted. Instead, the syringe needle 2 and the inner tube 3 are integrally formed, that is, the syringe needle 2 and the inner tube 3 form a complete stainless steel tube. The stainless steel tube serves as the inner tube 3, an end part of the stainless steel tube is a needle tip used as the syringe needle 2. The propulsive force may be better transferred by replacing the inner tube and the syringe needle with a complete stainless steel tube.

An elastomer 8 is a spring, and a support tube 7 may be arranged between the elastomer 8 and the casing 10.

The injection plunger rod 11 is provided with a protruding trigger 111 on which a locking plug 112 is arranged, and the locking plug 112 is provided with a one-way check rack 113.

The injection plunger rod 11 is provided with an anti-twist body 110 connected with the casing 10 in a sliding manner.

The anti-twist body 110 is non-circular. It may be square or polygonal. It may also comprise a chute and a guide rail, for preventing the injection plunger rod 11 and the casing 10 from relatively sliding in the radial direction, and ensuring the injection plunger rod 11 and the casing 10 to move in the axial direction only.

The locking socket 13 comprises a slot 130, an arched elastomer 131 located above the slot 130, a platy-elastomer 132 located below the slot 130 and slot wings 133, and the arched elastomer 131 and the platy-elastomer 132 are connected with each other by the slot wings 133 arranged on two sides. The platy-elastomer 132 is provided with a check hook 134, and clearance slots are arranged on the two sides of the platy elastomer 132.

The locking plug 112 may be inserted into and ejected from the slot 130. The slot 130 is formed by a semi-open space surrounded by the arched elastomer 131, the platy elastomer 132 and the slot wings 133, which are integrally formed with the casing 10. The clearance slots are arranged on the two sides of the platy elastomer 132, contributing to deform the platy elastomer 132 and the platy elastomer 132 when pressed. After the locking plug 112 is inserted into the locking socket 13, the one-way check rack 113 and the check hook 134 are engaged with each other. Because the one-way check rack 113 is provided with multiple one-way check teeth 113a, adjustment and positioning of the extension depth of the injection plunger rod 11 may be achieved, thus controlling the length of the syringe needle 2 extending out. After the arched elastomer 131 is pressed down by a finger of an operator, it applies a pressure to the platy elastomer 132 in the aid of the slot wings 133. The check hook 134 on the platy elastomer 132 is disengaged from the one-way check rack 113. The injection plunger rod 11 is rebounded to the original position under the action of the elastomer 8, and the syringe needle is retracted into the inner tube.

The arched elastomer 131 is provided with a release button 135. The release button 135 is of a concave structure, which is convenient to press the button down by a finger, additionally with a non-slip effect.

A tail end of the outer tube 4 is provided with a front end cap 1. The front end cap 1 and the outer tube 4 form an integrated structure or a split structure.

Figure 9:
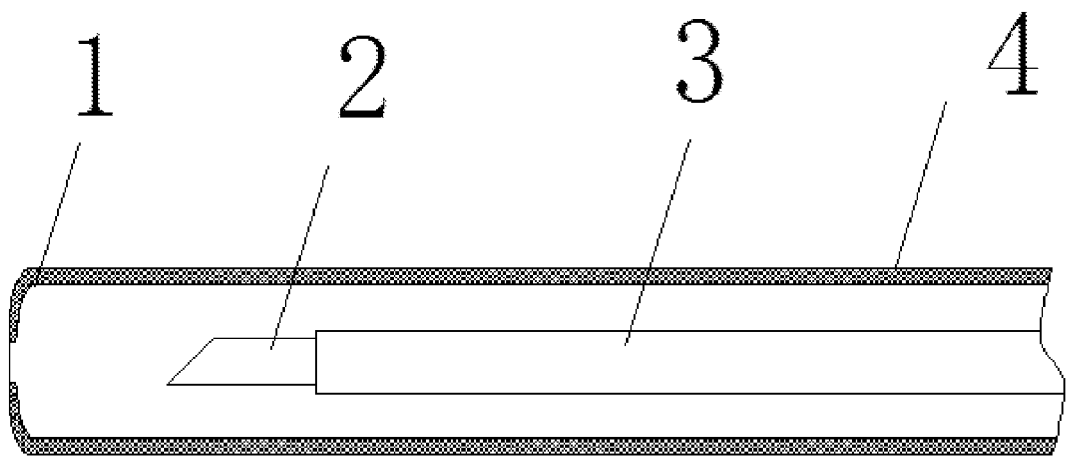

As shown in FIG. 9, the tail end of the outer tube 4 may also be an enclosed structure, and is provided with a small hole from which the syringe needle may be fed or retracted.

A tail end of the injection plunger rod 11 is provided with a syringe adapter 12 which is a Luer adapter.

The disposable remote-injection syringe for use with an endoscope of the invention further comprises a spring tube 15 arranged on an inner side of the outer tube 4.

The disposable remote-injection syringe for use with an endoscope of the invention further comprises a needle spring 14 arranged on a far end of the inner tube 3 and sleeved on the syringe needle 2.

The disposable remote-injection syringe for use with an endoscope of the invention further comprises a needle spring 14 arranged on the front end cap 1.

The needle spring 14 of the invention has the following functions.

(1) Due to a tortuous and complicated structure of the alimentary tract, the far end of the remote-injection syringe is in a tortuous state when in the alimentary tract. When the syringe needle extends out, it is easy to pierce through the outer tube to injure patients. Sheathing the syringe needle inside the spring may avoid such accidents mentioned above.

(2) The axial bending of the needle spring is flexible, thus contributing to the syringe moving forward in the tortuous alimentary tract.

The needle spring 14 of the invention has the following functions.

(1) Due to a tortuous and complicated structure of the alimentary tract, the far end of the remote-injection syringe is in a tortuous state when in the alimentary tract. When the syringe needle extends out, it is easy to pierce through the outer tube to injure patients. Sheathing the syringe needle inside the spring may avoid such accidents mentioned above.

(2) The syringe is coiled and then placed in a packaging bag. The syringe needle may extend out the outer tube a little in a nature state or a transport test, thereby damaging the packaging bag and the sterile state of the syringe, or, damaging the syringe needle and degrading the piercing performance. Spring can resist against the syringe needle, so that the syringe needle will not extend out unless a person applies a force to the handle.

(3) The axial bending of the needle spring is flexible, thus contributing to the syringe moving forward in the tortuous alimentary tract.

Usage of the disposable remote-injection syringe for use with an endoscope of the invention 1. The injection syringe is used in accompany with the endoscope. Before injection, an injector filled with injection is connected to an injection interface to inject the injection, in order to exhaust air in the injection tube and rinse the injection tube.

2. The injection syringe is inserted into a working channel of the endoscope, and slowly extended into the human body cavity through the endoscope channel under the surveillance of the endoscope. It must be ensure that the outer tube of the injection syringe is partially exposed from the far end of the endoscope channel.

3. The endoscope is adjusted to be in the best position, to make the injection syringe accurately reach to the position to be injected.

4. The handle is operated to make the syringe needle of the injection syringe extend out the outer tube and inject according to actual requirements.

5. At the end of injection, the syringe needle of the injection syringe is retracted to the outer tube, and the injection syringe is pulled out from the working channel of the endoscope.

The embodiments mentioned above just describe the preferred implementation ways of the invention, and will not form any limit to the concept and scope of the invention. Without deviating from the design concept of the invention, for an ordinary person skilled in the art, the technical solutions of the invention may have various modifications and improvements, and these modifications and improvements should fall into the protection scope of the invention. All of the technical contents claimed by the invention have been defined in the claims.

The invention claimed is:

1. A disposable remote-injection syringe for use with an endoscope, comprising:
   a syringe needle;
   an inner tube;
   an outer tube;
   a casing, the syringe needle installed on one end of the inner tube, the inner tube installed in the outer tube, the outer tube connected with the casing,
   an injection plunger rod, one end of which extending into the casing to be connected with the casing in a sliding manner;
   an elastomer connected with the injection plunger rod installed in the casing;
   a locking socket installed on the casing; and
   a locking plug connected with the locking socket in an engaging manner and installed on the injection plunger rod, the locking plug including a one-way check rack, the one-way check rack having a plurality of one-way check teeth arranged one after another along an axial direction of the injection plunger rod, wherein different one-way check teeth, when engaged with the locking socket, expose different lengths of the syringe needle from the outer tube.

2. The disposable remote-injection syringe according to claim 1, wherein the outer tube is connected with the casing via a positioning cap, and one end of the positioning cap is installed in the casing while another end thereof is connected with a sheath (5) sleeved outside the outer tube.

3. The disposable remote-injection syringe according to claim 2, wherein a tail end of the injection plunger rod is provided with a syringe adapter.

4. The disposable remote-injection syringe according to claim 1, wherein another end of the inner tube is connected with the injection plunger rod via a boosting tube.

5. The disposable remote-injection syringe according to claim 4, wherein a tail end of the injection plunger rod is provided with a syringe adapter.

6. The disposable remote-injection syringe according to claim 1, wherein the injection plunger rod includes a protruding trigger on which the locking plug is installed.

7. The disposable remote-injection syringe according to claim 6, wherein a tail end of the injection plunger rod is provided with a syringe adapter.

8. The disposable remote-injection syringe according to claim 1, wherein the injection plunger rod is provided with an anti-twist tube connected with the casing in a sliding manner.

9. The disposable remote-injection syringe according to claim 8, wherein a tail end of the injection plunger rod is provided with a syringe adapter.

10. The disposable remote-injection syringe according to claim 1, wherein the locking socket comprises a slot, an arched elastomer located above the slot, a platy-elastomer located below the slot and slot wings, the arched elastomer and the platy-elastomer being connected with each other by the slot wings installed on two sides, the platy-elastomer being provided with a check hook, and clearance slots being installed on the two sides of the platy-elastomer.

11. The disposable remote-injection syringe according to claim 10, wherein the arched elastomer is provided with a release button.

12. The disposable remote-injection syringe according to claim 11, wherein a tail end of the injection plunger rod is provided with a syringe adapter.

13. The disposable remote-injection syringe according to claim 10, wherein a tail end of the injection plunger rod is provided with a syringe adapter.

14. The disposable remote-injection syringe according to claim 1, wherein a tail end of the outer tube is provided with a front end cap, and the front end cap and the outer form an integrated structure or a split structure.

15. The disposable remote-injection syringe according to claim 14, wherein a tail end of the injection plunger rod is provided with a syringe adapter.

16. The disposable remote-injection syringe according to claim 14, wherein the disposable remote-injection syringe for use with an endoscope further comprises a needle spring installed on the front end cap.

17. The disposable remote-injection syringe according to claim 1, wherein a tail end of the injection plunger rod is provided with a syringe adapter.

18. The disposable remote-injection syringe according to claim 1, wherein the disposable remote-injection syringe for use with an endoscope further comprises a spring tube installed on an inner side of the outer tube.

19. The disposable remote-injection syringe according to claim 1, wherein the disposable remote-injection syringe for use with an endoscope further comprises a needle spring installed on a far end of the inner tube and sleeved on the syringe needle.

* * * * *